United States Patent [19]

Beckenbaugh et al.

[11] Patent Number: 4,784,661

[45] Date of Patent: Nov. 15, 1988

[54] TOTAL WRIST PROSTHESIS

[76] Inventors: Robert Beckenbaugh, 3015 Valleywood Dr., S.W., Rochester, Minn. 55902; Ted Bolinger, R.R. 8, Box 78; Dave Cox, R.R. 9, Box 72, both of Warsaw, Ind. 46580

[21] Appl. No.: 801,042

[22] Filed: Nov. 22, 1985

[51] Int. Cl.$^4$ .............................................. A61F 2/42
[52] U.S. Cl. ..................................................... 623/21
[58] Field of Search ...................... 623/21, 22, 23, 16, 623/18

[56] References Cited

U.S. PATENT DOCUMENTS

| | | | |
|---|---|---|---|
| 3,879,767 | 4/1975 | Stubstad | 623/21 |
| 3,909,853 | 10/1975 | Lennox | 623/21 |
| 4,063,314 | 12/1977 | Loda | 623/21 |
| 4,106,128 | 8/1978 | Greenwald | 623/21 |
| 4,164,793 | 8/1979 | Swanson | 623/21 |
| 4,178,640 | 12/1979 | Buechler et al. | 623/21 |
| 4,180,871 | 1/1980 | Hamas | 623/21 |
| 4,229,840 | 10/1980 | Gristina | 623/21 |
| 4,229,841 | 10/1980 | Youm | 623/21 |
| 4,259,752 | 4/1981 | Taleisnik | 623/21 |
| 4,261,062 | 4/1981 | Amstutz et al. | 623/19 |
| 4,307,473 | 12/1981 | Weber | 623/21 |
| 4,352,212 | 10/1982 | Greene et al. | 623/21 |

OTHER PUBLICATIONS

Youm et al., "Kinematics of the Wrist", The Journal of Bone and Joint Surgery, vol. 60-A, No. 4, Jun. 1978, pp. 423-432.
Huff et al., "Myelodysplasia", The Journal of Bone & Joint Surgery, 1978, p. 432.
Cooney, III, "Total Wrist Arthroplasty", Clinical Orthopaedics and Related Research, No. 1987, Jul./Aug. 1984, pp. 121-128.

Primary Examiner—Richard J. Apley
Assistant Examiner—David J. Isabella
Attorney, Agent, or Firm—Woodard, Emhardt, Naughton, Moriarty & McNett

[57] ABSTRACT

A total wrist prosthesis which has a metacarpal component and a radial component having ellipsoidal articulating surfaces. The metacarpal component and the radial component each have a fixation stem for insertion into the third metacarpal and the radius respectively. The fixation stem of the metacarpal component is curved dorsally to volarly so as to approximate the natural curvature of the third metacarpal and capitate of the human hand. The fixation stem of the metacarpal component has a center line which attaches to the head of the metacarpal component which contains the articulating surface dorsally from the minor axis of the ellipsoidal articulating surface. The fixation stem and the head of the metacarpal component have a plurality of wings attached thereto and a spur to prevent rotation of the device once inserted into the metacarpal. Also, the surface area of the metacarpal component proximal to the ellipsoidal articulating surface is coated with porous coating to aid in cement fixation.

The radial component of the wrist prosthesis also has a fixation stem which is fixedly attached to a holder which receives a bearing member that defines a concave ellipsoidal articulating surface which is complimentary to the convex articulating surface of the metacarpal component. The center line of the fixation stem of the radial component is displaced dorsally from the minor axis of the concave articulating surface and also radially from the minor axis. A porous coating is also present about the base of the holder and the fixation stem. The curvature of the metacarpal fixation stem and the displacement of the center lines of both fixation stems relative to the minor axis of the ellipsoidal surfaces to which they are attached cause the center of rotation and flexion-extension motion and radial-ulnar-deviation to approximate the natural centers of rotation of flexion-extension motion and radial-ulnar-deviation.

25 Claims, 5 Drawing Sheets

TOTAL WRIST PROSTHESIS

BACKGROUND OF THE INVENTION

1. Field of the Invention

This invention relates to a mechanical device for surgical replacement of certain bones, joints, and associated ligaments in a diseased or otherwise damaged human wrist, and more particularly to a total wrist prosthesis.

2. Information Disclosure Statement Pursuant to 37 CFR §1.97

Total wrist arthroplasty involves the prosthetic replacement of the wrist by an artificial joint designed to simulate normal wrist motion. Prosthetic replacement of the wrist requires careful consideration of anatomic and mechanical factors, appreciation of the techniques of implant fixation, and recognition of soft tissue balance across the wrist. Current cemented wrist implant designs have an unacceptably high rate of failure (15% to 30%) with a 5-year progressively decreasing "survival rate". See for example Cooney W. P., Beckenbaugh, R. D., Linscheid, R. L.: Total Wrist Arthroplasty-Problems with Implant Failures. Clin. Orth. Rel. Research 187: 121–128, 1984 (a copy of which is sent herewith).

Drawing kinematics of the wrist are very complex as depicted by Youm et al. Youm, Y. McMurtry, R. Y., Flatt, A. E., and Gillespie, T. E.: Kinematics of the Wrist, 1. An Experimental Study of the Radial-Ulnar Deviation and Flexion--Extension. J.Bone Joint Surg. 60A: 423, 1978. These motions could not be simply reproduced and incorporated in the design of a joint prosthesis. Based upon experience with previous wrist arthroplasties, and several key anatomic and kinematic principles found in the literature, a successful compromise is achieved by the present invention. In studies of healthy individuals with normal wrists, the center of rotation of the wrist has been found to be located within the head of the capitate. For radial-ulnar deviation (R-U-D), the center of rotation lies toward the ulnar side of the axis of the third metacarpal and the axis of the distal radius. The Center of flexion-extension motion (F-E-M) of the wrist was known to be offset toward the palm (volarly) from the axis of the third metacarpal and the distal radius, and also located in the head of the capitate. Pronation and supination are rotation motions of the arm about a longitudinal axis. The wrist does not rotate significantly in relation to the radius. The wrist has therefore been described as a biaxial joint with two degrees of freedom, F-E-M and R-U-D.

Furthermore, the index finger and the long metacarpals together with the capitate and lesser multangular form a "fixed unit." Very little relative motion occurs between these bones during all natural positions of F-E-M or R-U-D. Also, the head of the capitate contains the dual centers of rotation for both F-E-M and R-U-D. The capitate-third metacarpal fixed unit is therefore the logical positioning choice for the metacarpal component of the wrist prosthesis. The ellipsoidal head design of the present invention is further based upon the anatomy of the scaphoid-lunate-triquetrum unit. The proximal aspects of these bones, along with the interosseous ligaments, are covered by cartilage to form a continuous surface that move as a unit in R-U-D. The more anatomic ellipsoidal shape articulating component along with the appropriately shaped radial component in this device better approximates the function of the normal wrist joint than previous prosthetic designs.

Many variations and types of wrist prostheses have appeared and representative examples of these variations and types are disclosed by the following group of patent references. Each reference pertains in one way or another to a wrist prosthesis, though some references are believed to be more relevant to the present invention than others.

| Patent No. | Patentee |
|---|---|
| 4,259,752 | Taleisnik |
| 4,180,871 | Hamas |
| 4,063,314 | Loda |
| 4,106,128 | Greenwald, et al |
| 3,909,853 | Lennox |
| 4,307,473 | Weber |
| 4,352,212 | Greene, et al |
| 4,229,840 | Gristina |
| 4,229,841 | Youm, et al |
| 4,178,640 | Buechler, et al |
| 4,164,793 | Swanson |

Taleisnik discloses a prosthetic wrist joint having an "ovoid" head on the metacarpal component. Taleisnik also discloses a prosthesis with a single metacarpal fixation stem and a single radial fixation stem, wherein the radial fixation stem in the radial component is offset relative to the receiving surface of the radial component so as to shift the center of rotation ulnarlly and volarly. Taleisnik, however, discloses only a semi-cylindrical receiving surface in the radial component and thus the receiving surface is not complementarily shaped relative to the bearing surface, as is the case in the present invention.

Hamas depicts a wrist prosthesis in which the concave member is carried by the metacarpal component with the bearing head being carried by the radial component. Hamas pertains to a wrist prosthesis which has the axes of radial-ulnar deviation and of flexion-extension motion located in specific relationships. The general displacement of these axes from the radial axis and the metacarpal axis are generally in the same direction as contemplated by the present invention.

The remaining patents are of less interest. The Loda, Greenwald and Lennox patents all show a ball and socket combination used in the wrist joint with the ball member in each instance being carried by the metacarpal component. The Loda patent claims a prosthesis which includes a primary stem which extends from the ball or "rotulla" as it is called in the patent, and a secondary stem which extends outwardly from the primary stem and then is bent into a parallel relationship with the primary stem. The Greenwald patent describes a prosthesis which includes a ball on the end of the metacarpal component and received within a cup-shaped member which is in turn received by the radial component. The Lennox patent describes a more narrow concept in which the metacarpal components are rotatable relative to a carpal or intermediate component which is in turn rotatable relative to the radial component. Each of the Weber and Greene patents shows a cylindrical head of the metacarpal component received within a cylindrical recess of the radial component. The Gristina and Youm patents both show dual pivoting members, as does the Weber patent previously cited. The Buechler and Swanson patents are of only general interest and not directly related to the present invention.

The invention disclosed in this application is basically a biaxial unit. The stem of the radial component is offset so that the center of R-U-D is shifted ulnarward to correspond with the anatomic center of rotation of the normal wrist. Similarly, the radial stem is offset so that the center of F-E-M lies volar to the mid-shaft of the radius. In contrast, the Hamas device has a spherical approximation of a biaxial anatomic structure, and therefore does not and cannot separate the centers of rotation for F-E-M and R-U-D. Other wrist prostheses do not correctly approximate either center of rotation. As was previously stated, the design of the present invention is a successful compromise of several key anatomic and kinematic principles.

SUMMARY OF THE INVENTION

The improved wrist prosthesis according to the present invention is characterized by the fact that the metacarpal articulating surface and the radial articulating surface are ellipsoidal and are complementarily shaped with respect to each other. The wrist prosthesis has two fixations stems, one for the metacarpal component and one for the radial component for insertion into the third metacarpal and the radius.

It is an object of the present invention to design a prosthesis which simulates the function of the normal wrist in both radial-ulnar-deviation and flexion extension motion.

An additional object of this invention is to provide a wrist prosthesis which restores normal carpal height. Yet another object of the present invention is to reestablish balance of the wrist with proper implant sizing in prosthesis configurations.

Additionally, it is an object of the present invention to provide a device with larger, more anatomically shaped bearing surfaces and stems which better distribute the loads throughout the metacarpal and radial components, thus reducing the incidence of loosening of the prosthesis by lowering the repetitive stresses acting on the bone cement and or cement prosthesis interface.

A further object of the present invention is to increase the articular surface area of contact as compared to previous prosthesis designs, thus reducing stress concentration and surface wear along the articulating surfaces.

Additionally, another object of the present invention is to design a device that approximates the natural center of rotation of the wrist and in case of failure permits acceptable salvage procedures.

Related objects and advantages of the present invention will be apparent from the following description.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figures 1, 2:
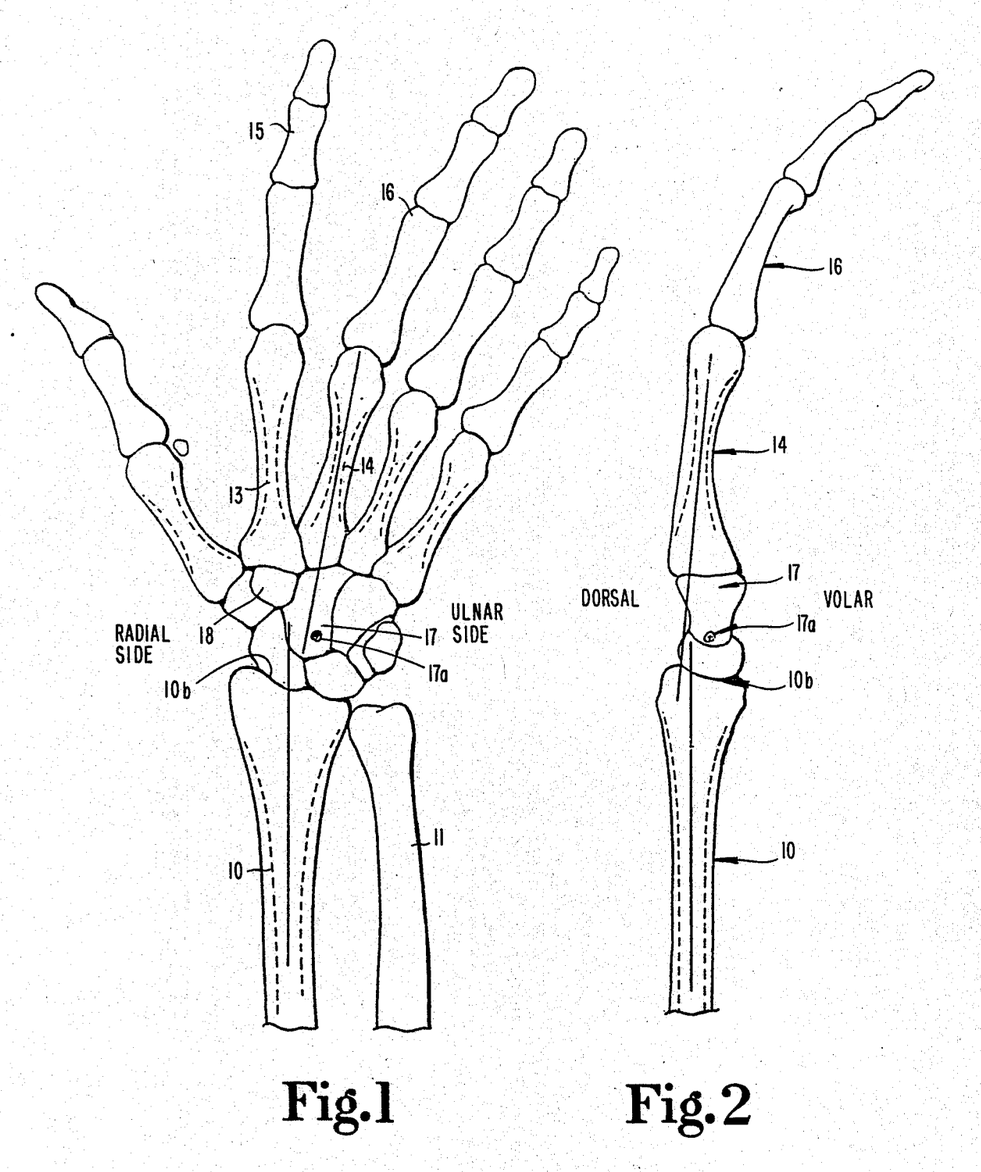
FIG. 1 is a schematic posterior-anterior view of the skeleton of a right wrist and hand.
FIG. 2 is a schematic, lateral view of the skeleton of a wrist observed with a number of bones omitted for clarity.

Referring now to FIG. 1 there is shown in profile a healthy right wrist skeleton. The hand is supported by two bones, the radius 10 and the ulna 11. These bones bear upon each other at their distal extremities, and the distal face of the radius comprises an important articular surface 10b.

FIG. 1 also illustrates the bones in the hand including the second metacarpal 13 and the third metacarpal 14 which are just behind the index 15 and middle finger 16, respectively. Eight carpal bones (the carpus) are shown between the articular surface 10b of the radius and the metacarpals. The capitate 17 is fixed relative to the third metacarpal 14. These two bones move as a unit to define the plane of the hand in both flexion-extension and radial-ulnar-deviation. Also at the base of the second metacarpal 13 is a carpal known as the trapezoid 18.

The two axes of wrist motion are known to pass through an area known as the "head" 17a of the capitate 17. As noted in FIG. 1, the radial side of the wrist is the side on which the radius 10 is located, while the ulnar side is the side on which the ulna 11 is located. FIG. 2 illustrates that the dorsal side of the wrist is the side corresponding to the back of the hand, while the volar or palmar side of the wrist is at a side corresponding to side of the palm of the hand.

Figure 3:
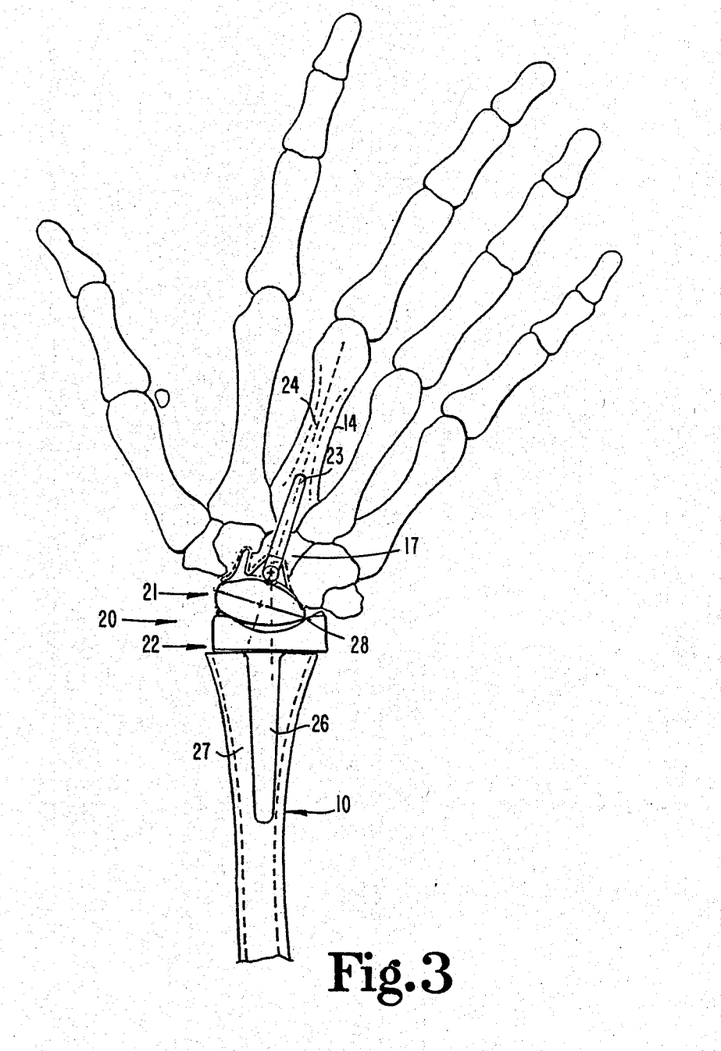
FIG. 3 is a schematic posterior-anterior view of the skeleton of a right wrist with a prosthesis according to the present invention inserted therein.
Figure 4:
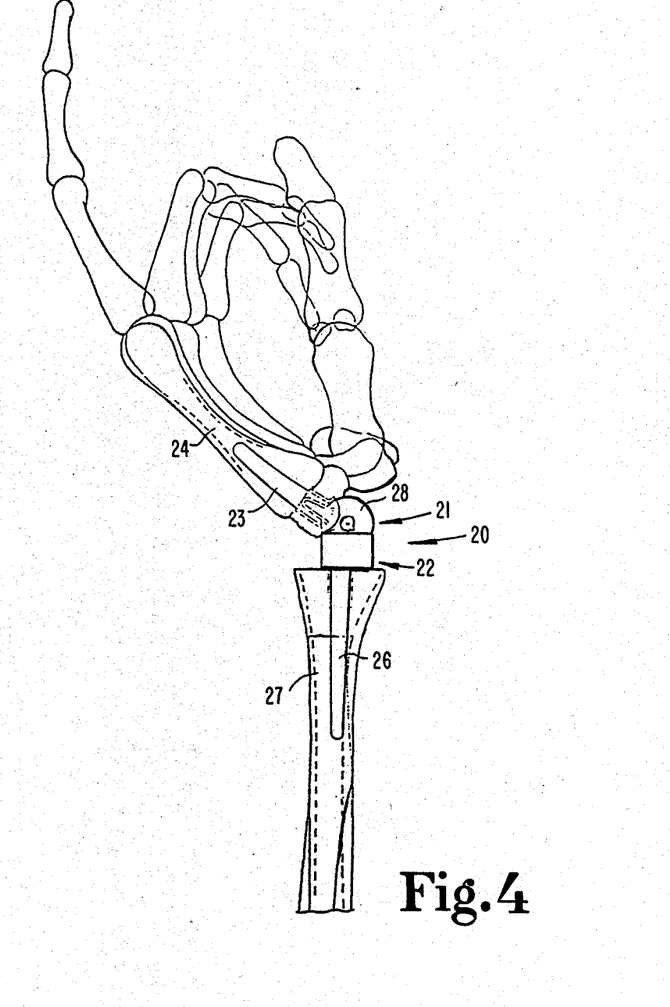
FIG. 4 is a schematic, lateral view of the skeleton of the wrist as observed with the prosthesis of the present invention inserted therein.
Figure 5:
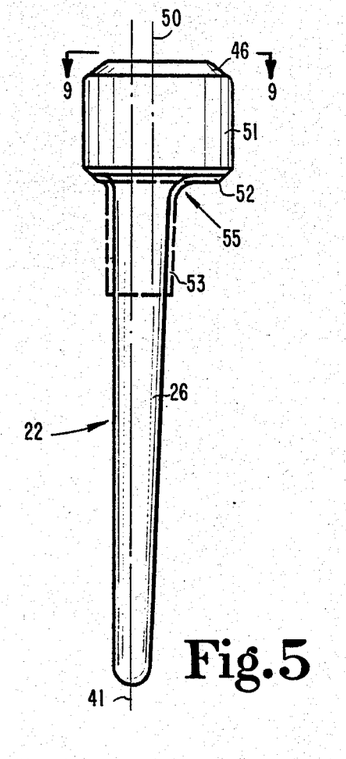
FIG. 5 is an ulnar side view of a preferred embodiment of the right radial component of the wrist prosthesis of the present invention.
Figure 6:
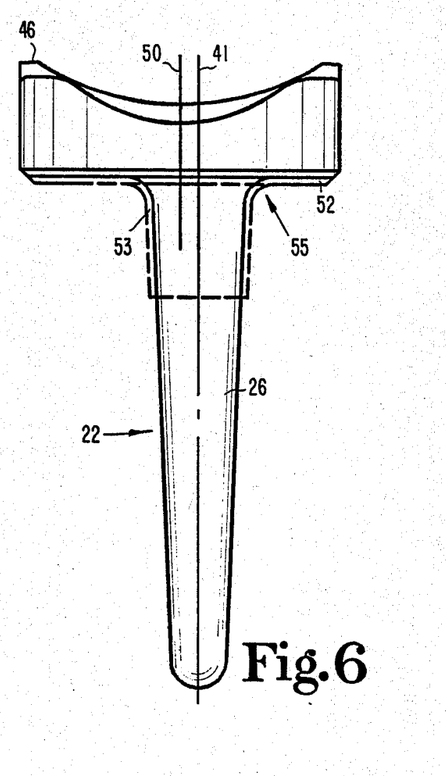
FIG. 6 is a volar side view of the right radial component shown in FIG. 5.

Referring now, more particularly, to FIGS. 3 and 4 there is illustrated a wrist prosthesis 20 positioned within a human wrist. The basic procedure employed in the implantation of the wrist prosthesis of the present invention is known in the art and does not differ substantially from other procedures applicable with prior art devices. Since these procedures are known to persons skilled in the art and do not form a part of the present invention, details for the procedure are not necessary to a full description of the present invention and are not provided herein. As can be noted from FIGS. 3 and 4, in locating the prosthesis in position several of the carpals are removed from the hand and the radius 10 and ulna 11 are resected. This removal of the carpals and resectioning of the radius and ulna is similar to that carried out in other wrist prosthesis operations.

From the drawings it can be seen that the wrist prosthesis 20 includes a metacarpal component 21 and a radial component 22. The metacarpal component has a fixation stem 23 which is located through the capitate 17 and into the medulla 24 of the third metacarpal 14. The radial component 22 also has a fixation stem 26 which is located in the medulla 27 of the radius 10.

Figure 9:
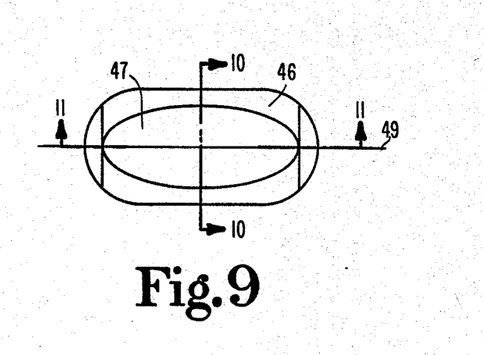
FIG. 9 is an end view of the preferred embodiment of the right metacarpal component taken in the direction of line 9—9 in FIG. 5.
Figure 10:
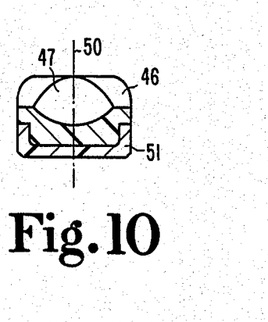
FIG. 10 is a a cross-sectional view of the metacarpal component of FIG. 9, taken along the line 10—10 and looking in the direction of the arrows.
Figure 11:
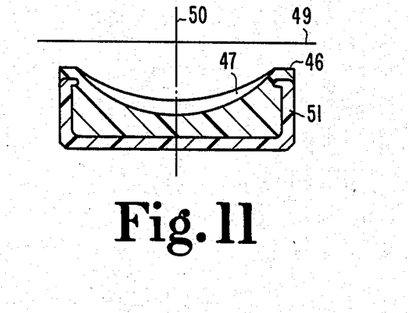
FIG. 11 is a cross-sectional view of the metacarpal component of FIG. 9, taken along the line 11—11 and looking in the direction of the arrows.
Figure 12:
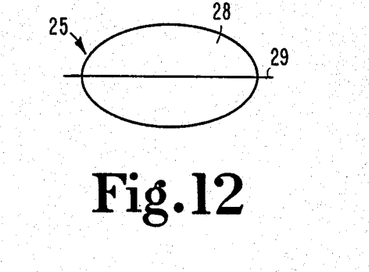
FIG. 12 is a left end view of the metacarpal component of FIG. 7 showing in particular the convex articulating surface.

As shown in the preferred embodiment, the metacarpal component has a convex, ellipsoidal articulating surface 28 which is pivotally received within a concave ellipsoidal articulating surface 47 (FIGS. 9-11) of the radial component when the device is inserted into the wrist. Alternatively, the components could be reversed to have the radial component include the convex, ellipsoidal articulating surface which would be pivotally received within a concave, ellipsoidal articulating surface of the metacarpal component when the parts are inserted in the wrist.

Referring to FIGS. 7, 8 and 12 through 14, the preferred embodiment of the metacarpal component 21 of the wrist prosthesis 20 will be more particularly described. The metacarpal component 21 includes a fixation stem 23 attached to a head portion 25, the head portion 25 defining an ellipsoidal articulating surface 28. The ellipsoidal articulating surface has a first major axis 29 and a first minor axis 30.

The metacarpal component may be formed from a variety of materials suitable in strength, durability and biocompatibility. Preferably the head portion 25 and the fixation stem 23 are integrally formed. A variety of materials are known in the art to be suitable for this type of prosthesis. The ellipsoidal articulating surface 28 may similarly be formed from many different materials, and a preferred material is cobalt chromium alloy. It is also envisioned that the ellipsoidal articulating surface could be made of such alternative materials as cobalt-chromium alloy, ceramic, delrin,, or polyethylene as well as other metal alloys or implant ceramics.

Figure 13:
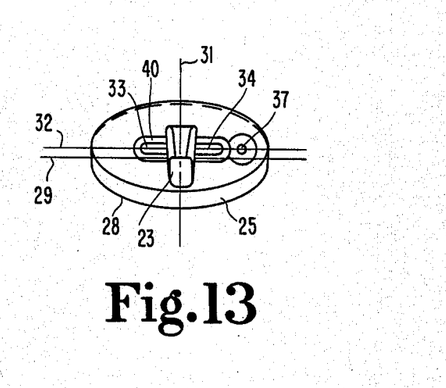
FIG. 13 is a right end view of the metacarpal component along the line 13—13 of FIG. 7.

Fixation stem 23 is fixedly attached to the head portion 25 defining the ellipsoidal articulating surface 28. Fixation stem 23 has a center line 31 which extends through the center of the fixation stem. FIG. 13 illustrates that at the point of contact of the fixation stem 23 with the articulating surface 28 a projection line 32 which is parallel to the first major axis 29 and intersects center line 31 of the fixation stem at right angles is displaced dorsally from the center line 19. It is envisioned that three different sizes of the metacarpal component 21, as well as the radial component 22, would provide a desirable range of sizes to accommodate various applications of the prosthesis. The amount of displacement between protection line 32 and center line 29 varies according to which size prosthesis is involved.

This displacement of projection line 32 of center line 31 of stem 23 aids in shifting the center of flexion-extension-motion of the ellipsoidal articulating surface 28 volarly so as to approximate the normal center of flexion-extension-motion in the human wrist.

Figure 7:
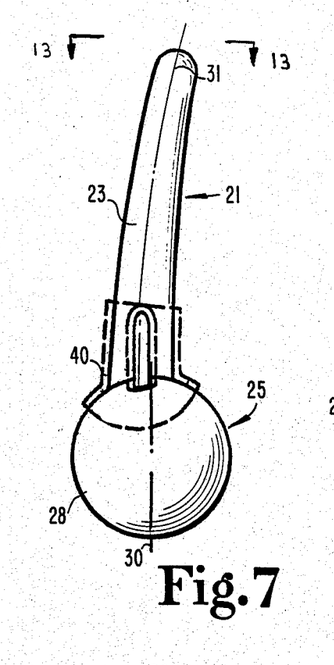
FIG. 7 is an ulnar side view of the right metacarpal component of a preferred embodiment of the wrist prosthesis of the present invention.
Figure 8:
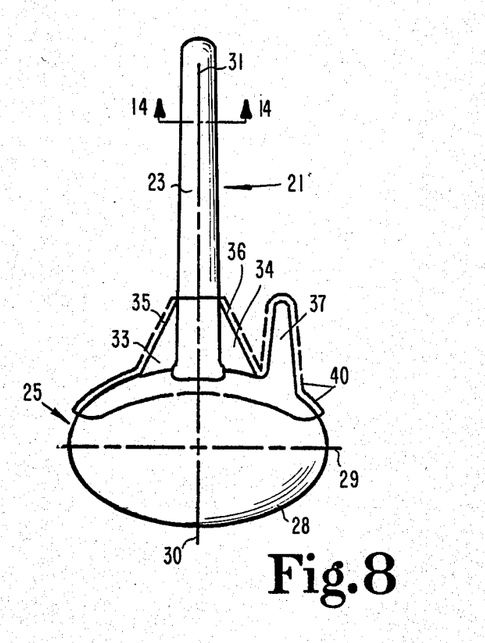
FIG. 8 is a volar side view of the right metacarpal component shown in FIG. 7.

As is illustrated in FIGS. 7 and 8, center line 31 when viewed from the ulnar side is curved, while when viewed from the volar side is straight. Thus, it is apparent that stem 23 curves dorsally to volarly in this preferred embodiment. The curvature of stem 23 dorsally to volarly approximates the normal curvature of the third metacarpal and capitate. Thus, the amount of curvature varies between the three different sizes of wrist prosthesis envisioned. However, when viewed from the volar side, the fixation stem 23 and the center line 31 are straight and, therefore, it is shown that stem 23 preferably attaches to ellipsoidal articulating surface 28 so that stem 23 extends along the first minor axis of ellipsoidal articulating surface 28. However, as was previously described, fixation stem 23 is dorsally offset from the dorsal and volar center of ellipsoidal articulating surface 28.

Figure 14:
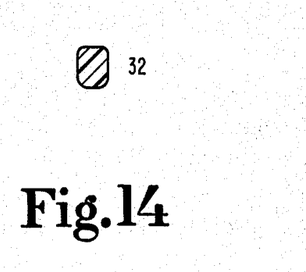
FIG. 14 is a cross-sectional view of the stem portion of the metacarpal component of FIG. 7, taken along the line 14—14 and looking in the direction of the arrows.

Also as is illustrated in FIG. 7 and FIG. 8, fixation stem 23 has a slight taper from wide to narrow as the distance from the connection with the head portion 25 is increased. The length of the fixation stem is sufficient to extend through part of the capitate and a significant amount into the third metacarpal as is illustrated in FIG. 4. FIG. 14 illustrates that the cross section 32 of the fixation stem 23 is non-circular and in the illustrated embodiment approximates a rectangle. The non-circular cross section 32 of fixation stem 23 is intended to prevent loosening and rotation of the metacarpal component once inserted into the third metacarpal.

Referring more particularly now to drawings 8 and 13 there are illustrated a plurality of wings 33 an 34 which are fixedly attached to the fixation stem 23 and centered about projection line 32. It is envisioned that these wings 33 and 34 may have razor sharp edges 35 and 36 to aid in the insertion of these wings into the capitate when the metacarpal component 21 is inserted through the capitate 17. These wings are intended to increase the stability of the prosthesis when it is inserted in the wrist. Also spur 37, which is centered on projection line 32 is provided for insertion into the trapezium in order to prevent rotation of the prosthesis when inserted in the wrist. It is envisioned that wings 33 and 34 and spur 37 will be integrally joined with head portion 25 and fixation stem 23 to form metacarpal component 21. Referring more particularly to FIG. 7 and FIG. 8, it can be seen that the surface area of the metacarpal component 21 proximal to the convex articulating surface 28 is covered with a porous coating 40. This porous coating is designed to enhance cement fixation of the prosthesis and increase the strength of the cement bond formed when the metacarpal component is inserted through the capitate and into the metacarpal.

Referring to FIGS. 5, 6 and 9 through 11, there is illustrated the metacarpal component 22. Metacarpal component 22 consists of a support member 55 and a bearing member 26. The support member 55 includes second fixation stem 26 and holder 51 which are fixedly attached to one another. It is envisioned that in the preferred embodiment the support member 55 will be constructed of a variety of materials which were proved suitable in previous prosthetic devices. Preferably support member 55 will be constructed of a cobalt chromium alloy. Bearing member 46 will also be constructed of materials that were proved suitable in previous wrist prosthesis, with the preferable material being ultra high molecular weight polyethylene. Use of polyethylene for the bearing member in the insertion of the bearing member within the holder 51 aids in the prevention of cold flow that has been observed in previous wrist prosthesis.

The concave, ellipsoidal articulating surface 47 has a second major axis 49 and a second minor axis 50. Second major axis 49 and the second minor axis 50 are colinear with the first major axis 29 and the first minor axis 30 when the metacarpal component is contiguosly received within the concave partial ellipsoidal articulating surface. The radial bearing surface component is received within a reception member 51. FIGS. 10, 11, 4 and 5 illustrate that the radial bearing component extends beyond the receiving member in the radial component 22. The radial bearing member 46 extends beyond the receiving member 51 in order to prevent metal to metal clicking which leads to fatigue and possible failure and wrist prosthesis.

Fixation stem 26 is fixedly attached to receiving member 51. Center line 41 of fixation stem 26 is displaced dorsally to second minor axis 50 at the point of connection of stem 26 to receiving member 50. Also center line 41 of stem 26 is displaced radially with respect to second minor axis 50. The dorsal displacement of center line 41 with respect to second minor axis 50 aids in moving the center of flexion-extension motion volarly as in the human wrist. The radial displacement of center line 41 with respect to second minor axis 50 aids in moving the center of radial and ulnar deviation ulnarward as occurs in the human wrist. Stem 26 tapers from wide to narrow as the distance from the point of connection to receiving member 51 increases. Stem 26 has a non-circular cross section similar to that illustrated in FIG. 14. A portion of fixation stem 26 and the base 52 of receiving member 51 have a porous coating 53 similar to that previously described with respect to the metacarpal component.

It is believed that the wrist prosthesis disclosed in this application will aid in curing many of the problems inherent in previous wrist prosthesis. Due to the ellipsoidal shape of ellipsoidal articulating surface 28 the radial end of the ellipsoidal articulating surface 28 provides a supporting bearing surface for the base at the trapezium, thus providing some enhanced stability to thumb function not found in other wrist prosthesis.

What is claimed is:

1. A total wrist prosthesis for implantation with the third metacarpal and the radius to provide an artificial wrist joint, comprising:
    a first component having a head portion defining an ellipsoidal, convex articulating surface and further including a first fixation stem fixedly attached to the head portion;
    a second component having a receptacle portion defining an ellipsoidal, concave articulating surface and further including a second fixation stem fixedly attached to the receptacle portion, said ellipsoidal, concave articulating surface being shaped complementary to the ellipsoidal, convex articulating surface of said first component;
    first fixation means for affixing the first fixation stem to one of the third metacarpal and the radius; and,
    second fixation means for affixing the second fixation stem to the other of the third metacarpal and the radius;
    the convex articulating surface of said first component being received adjacent the concave articulating surface of said second component when either said first fixation stem or said second fixation stem is received in the third metacarpal and the other of said first fixation stem or said second fixation stem is received in the radius.

2. The prosthesis of claim 1 in which the ellipsoidal, convex articulating surface of said first component is substantially congruous with the ellipsoidal, concave articulating surface of said second component.

3. The prosthesis of claim 1 in which said first component is configured to be received in the third metacarpal and said first fixation means is for affixing the first fixation stem to the third metacarpal, and further in which said second component is configured to be received in the radius and said second fixation means is for affixing the second fixation stem within the radius.

4. The prosthesis of claim 3 in which the ellipsoidal, convex articulating surface of said first component is substantially congruous with the ellipsoidal, concave articulating surface of said second component.

5. The prosthesis of claim 3 in which the ellipsoidal, convex articulating surface of said first component has a minor axis, the first fixation stem having a centerline offset dorsally from the minor axis of the convex articulating surface, and further in which the ellipsoidal concave articulating surface of said second component has a minor axis, the second fixation stem having a centerline offset dorsally from the minor axis of the concave articulating surface.

6. The prosthesis of claim 3 in which the centerline of the second fixation stem is offset radially from the minor axis of said concave articulating surface.

7. The prosthesis of claim 6 in which the ellipsoidal, convex articulating surface of said first component has a minor axis, the first fixation stem having a centerline offset dorsally from the minor axis of the convex articulating surface, and further in which the ellipsoidal concave articulating surface of said second component has a minor axis, the second fixation stem having a centerline offset dorsally from the minor axis of the concave articulating surface.

8. The prosthesis of claim 3 wherein said first component includes porous coated surface areas proximal to the convex articulating surface and wherein said second component includes porous coated surface areas proximal to the concave articulating surface, the porous coated surface areas providing enhanced cement fixation of said prosthesis.

9. The prosthesis of claim 3 wherein said first fixation stem has a radius of curvature that approximates the radius of curvature of the normal human third metacarpal and capitate.

10. The prosthesis of claim 9 wherein said first component includes porous coated surface areas proximal to the convex articulating surface and wherein said second component includes porous coated surface areas proximal to the concave articulating surface, the porous coated surface areas providing enhanced cement fixation of said prosthesis.

11. The prosthesis of claim 10 wherein said first component further comprises a wing attached to the first fixation stem and the head portion, and a spur fixedly attached to the head portion and configured for insertion into the trapezoid.

12. The prosthesis of claim 11 wherein said first fixation stem and said second fixation stem each have a non-circular cross section.

13. The prosthesis of claim 12 in which the ellipsoidal, convex articulating surface of said first component has a minor axis, the first fixation stem having a centerline offset dorsally from the minor axis of the convex articulating surface, and further in which the ellipsoidal concave articulating surface of said second component has a minor axis, the second fixation stem having a centerline offset dorsally from the minor axis of the concave articulating surface.

14. The prosthesis of claim 13 in which the centerline of the second fixation stem is offset radially from the minor axis of said concave articulating surface.

15. The prosthesis of claim 1 in which the second component includes a support member and a bearing member, the support member including the second fixation stem and further including a holder attached to the second fixation stem, the bearing member being received within and supported by the holder of the support member, the bearing member having the receptacle portion defining an ellipsoidal, concave articulating surface, said ellipsoidal, concave articulating surface being shaped complementary to the ellipsoidal, convex articulating surface of said first component.

16. The prosthesis of claim 15 in which the ellipsoidal, convex articulating surface of said first component is substantially congruous with the ellipsoidal, concave articulating surface of said second component.

17. The prosthesis of claim 16 in which said first component is configured to be received in the third metacarpal and said first fixation means is for affixing the first fixation stem to the third metacarpal, and further in which said second component is configured to be received in the radius and said second fixation means is for affixing the second fixation stem within the radius.

18. The prosthesis of claim 17 in which the ellipsoidal, convex articulating surface of said first component is substantially congruous with the ellipsoidal, concave articulating surface of said second component.

19. The prosthesis of claim 17 in which the ellipsoidal, convex articulating surface of said first component has a minor axis, the first fixation stem having a centerline offset dorsally from the minor axis of the convex articulating surface, and further in which the ellipsoidal concave articulating surface of said second component has a minor axis, the second fixation stem having a centerline offset dorsally from the minor axis of the concave articulating surface.

20. The prosthesis of claim 17 in which the centerline of the second fixation stem is offset radially from the minor axis of said concave articulating surface.

21. The prosthesis of claim 20 in which the ellipsoidal, convex articulating surface of said first component has a minor axis, the first fixation stem having a centerline offset dorsally from the minor axis of the convex articulating surface, and further in which the ellipsoidal concave articulating surface of said second component has a minor axis, the second fixation stem having a centerline offset dorsally from the minor axis of the concave articulating surface.

22. The prosthesis of claim 17 wherein said first component includes porous coated surface areas proximal to the convex articulating surface and wherein said second component includes porous coated surface areas proximal to the concave articulating surface, the porous coated surface areas providing enhanced cement fixation of said prosthesis.

23. The prosthesis of claim 17 wherein said first fixation stem has a radius of curvature that approximates the radius of curvature of the normal human third metacarpal and capitate.

24. The prosthesis of claim 17 wherein said first component further comprises a wing attached to the first fixation stem and the head portion, and a spur fixedly attached to the head portion and configured for insertion into the carpals.

25. The prosthesis of claim 17 wherein said first fixation stem and said second fixation stem each have a non-circular cross section.

* * * * *